United States Patent [19]

Nix et al.

[11] 4,304,854

[45] Dec. 8, 1981

[54] ALPHA-AMYLASE ASSAY AND SUBSTRATES FOR USE THEREIN

[75] Inventors: Paul T. Nix, Jackson, N.J.; Rebecca D. Goldfarb, Baltimore, Md.; Linda J. Stong, Hightstown, N.J.; Lorraine E. Sulick, Scotch Plains, N.J.; Ramesh C. Trivedi, Freehold, N.J.; Stanley W. Morgenstern, Neptune, N.J.

[73] Assignee: Worthington Biochemical Corporation, Freehold, N.J.

[21] Appl. No.: 165,035

[22] Filed: Jul. 1, 1980

Related U.S. Application Data

[63] Continuation-in-part of Ser. No. 80,672, Oct. 1, 1979, abandoned, which is a continuation of Ser. No. 912,986, Jun. 6, 1978, abandoned.

[51] Int. Cl.$^3$ .................. C12Q 1/54; C12Q 1/58; C12Q 1/40; C12P 19/18
[52] U.S. Cl. ..................... 435/14; 435/15; 435/22; 435/25; 435/26; 435/97; 435/95; 127/29
[58] Field of Search ............ 435/14, 15, 22, 25, 435/26, 805, 810, 97, 99, 95, 90, 101, 72; 424/2; 127/29, 32; 536/1, 102, 103

[56] References Cited

U.S. PATENT DOCUMENTS

2,891,869  6/1959  Langlors.
4,036,697  7/1977  Pierre et al. .................. 435/22

FOREIGN PATENT DOCUMENTS

2729636  2/1978  Fed. Rep. of Germany.

OTHER PUBLICATIONS

Gillard et al., "Amylo-1,6-Glucosidase/4-α-Glucanotransferase: Use of Reversible Substrate Model Inhibitors to Study the Binding and Active Sites of Rabbit Muscle Debranching Enzyme", Biochem., vol. 16, No. 18 (1977), pp. 3978–3987.
Marshall et al., "Detection of Endo-Acting Carbohydrases, Particularly in the Presence of Exoenzymes Acting on Same Substrate", Anal. Biochem., vol. 43, (1971), pp. 316–321.
Nix et al., "A New Method for Determination of α-Amylase", Clin. Chem., vol. 24, No. 6, (1978), p. 1000.
Swartz et al., "Escherichia coli maltodextrin phosphorylase", Chem. Abstracts, vol. 67, No. 19, (1967), p. 8257, Abs. No. 87876v.
Walker, et al., "The Mechanism of Carbohydrase Action", Biochem. J., vol. 76, No. 2, (1960), pp. 264–268.
Hestrin, "Action Pattern of Crystalline Muscle Phosphorylase", J. Biol., vol. 179, pp. 943–954.
Kruger, "Changes in The Amylases at Hand Spring Wheat During Growth and Maturation", Cereal Chem., vol. 49, No. 4, (1972), pp. 379–390.
Huang, et al., "A Specific Sensitive Assay for α-amylase Utilizing Modified Starch as Substrate", Clin. Chem., vol. 22, No. 7, (1976), p. 1164.
Richter, et al., "A Kinetic UV Method for the Determination of α-amylase", Clin. Chem., vol. 19, No. 6, (1973), p. 644.
Strenk, et al., "Substrate Starches in a U.V. Method for Quantitation of Amylase Activity", Clin. Chem., vol. 24, No. 6, (1978), p. 1000.
Kruger et al., "The Use of Reduced β-Limit Dextrin as Substrate i an Automated Amylase Assay," Cereal Chem., vol. 149, (1972), pp. 453–458.
Kerr, Chemistry and Industry of Starch, 2nd ed., (1950), Academic Press, Inc., N.Y., pp. 210, 212–214, 414.
Barman, Enzyme Handbook, Springer-Verlang, New York Inc., NY, (1969), pp. 302, 303, 562–564.
Bergmeyer, Methods of Enzymatic Analysis, Academic Press, Inc., N.Y. (1974), pp. 505–507, 890–894.

Primary Examiner—Thomas G. Wiseman
Attorney, Agent, or Firm—Kenyon & Kenyon

[57] ABSTRACT

A maltodextrin phosphorylase limit dextrin in the presence of maltodextrin phosphorylase and inorganic phosphate, is used as a substrate for alpha-amylase, which initiates a series of enzymatic reactions resulting in a chromogen response which can be used to measure the concentration of alpha-amylase in a body fluid. A novel limit dextrin and its preparation also are described.

14 Claims, No Drawings

ALPHA-AMYLASE ASSAY AND SUBSTRATES FOR USE THEREIN

This application is a continuation-in-part of Application Ser. No. 080,672 filed Oct. 1, 1979 abandoned, which in turn is a continuation of Application Ser. No. 912,986, filed June 6, 1978 abandoned.

This invention relates to reagents and methods for determining alpha-amylase concentration in a body fluid, such as plasma, serum, urine and saliva. It relates more especially to the detection and measurement of alpha-amylase using coupled enzymatic reactions and to the substrate for alpha-amylase that is used therein.

BACKGROUND

Alpha-amylase determinations are being resorted to with increasing frequency in clinical laboratories as an aid in diagnosing pancreatic and other diseases which alter normal concentration of alpha-amylase in a body fluid. Alpha-amylase is the common traditional name for the enzyme more precisely designated as alpha-1,4-glucan 4-glucanohydrolase.

Alpha-amylase plays a vital physiological role in enabling the digestion of starch and other polysaccharides by virtue of its specific enzymatic activity in the hydrolysis of alpha-1,4 linkages in the polysaccharide molecule, with the formation of maltose and various other oligosaccharides as ultimate products of the enzymatic reaction. Detection of abnormalities in the alpha-amylase content of body fluid provides an important aid in clinical diagnosis.

A number of analytical methods for the determination of alpha-amylase have been developed based upon the ability of alpha-amylase to hydrolyze starch. In all of these methods, starch or a starch derivative is digested with the sample containing alpha-amylase to be analyzed. Then the extent of the alpha-amylase induced degradation is measured by a variety of procedures. For example, the decrease in the amount of the starch substrate has been directly measured by an amyloclastic method, in which the decreased starch content is determined by adding iodine to the sample, and measuring the intensity of the blue colored starch-iodine complex which is formed. Alternatively, the decrease in starch content has been measured by the decrease in turbidity of an aqueous starch suspension following alpha-amylase digestion. Another chemical method for determining alpha-amylase activity involves use of a modified starch as the substrate, wherein the starch has a chromophore covalently linked to it. On digestion with alpha-amylase, small, water soluble colored fragments are formed, and the intensity of the color in the solution is measured photometrically.

Still another chemical analytical procedure is based upon reduction-oxidation analysis for reducing ends which are formed by the reaction of alpha-amylase with the starch substrate.

None of these chemical methods had proven entirely satisfactory for clinical use. All are time consuming, and require standard curves, while most also require the use of blanks, and long incubation times. Other problems include variability depending upon the source of the starch, sensitivities due to differences in laboratory technique and the need for specialized equipment.

Still other analyses are based upon enzymatic detection methods and, to date, all prior commercially available enzymatic alpha-amylase kits have been based upon measurements of the rate at which maltose is formed by the action of alpha-amylase on starch or an oligosaccharide substrate, such as maltotetraose or maltopentose. In one such analysis, maltose is converted to glucose by the enzyme alpha-glucosidase, and the level of glucose is in turn determined by conversion to glucose-6-phosphate by hexokinase, and conversion of glucose-6-phosphate to 6-phosphogluconate by reaction with beta-nicotinamide-adenine-dinucleotide (NAD) in the presence of glucose-6-phosphate dehydrogenase, as represented by the following sequence:

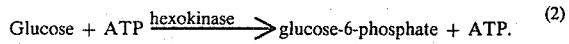
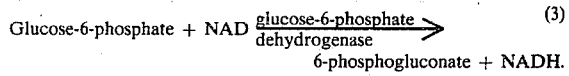

In this reaction system the conventional abbreviation NAD is used and is used elsewhere herein and in the claims, in reference to the coenzyme beta-nicotinamide-adenine-dinucleotide and NADH is used in reference to the same coenzyme in its reduced form. It also is to be understood that the NAD may be replaced by or used in admixture with NADP, namely, betanicotinamide-adenine-dinucleotide phosphate which in its reduced form is indicated as NADPH.

Still other procedures detect the formation of maltose via the enzyme maltose phosphorylase, as is illustrated by the following sequence:

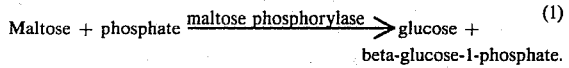
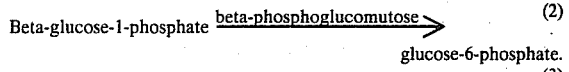
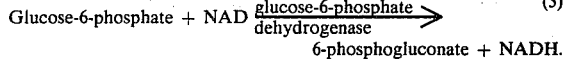

Typically, the increase in absorbence at 340 nm due to increased levels of NADH is measured photometrically. These methods still are not as accurate or as sensitive as may be desired.

Still more recently, it has been proposed to use as the substrate for the alpha-amylase a starch which has been subjected to partial oxidation, with resulting damaging random effect on alpha-1,4 linked glucoses of the starch molecule to form a so-called "blocked" starch. In such a "blocked starch", the reactivity of the damaged alpha-1,4 linkages in blocked to sufficient extent to inhibit the activity of an exocarbohydrase on the starch molecule, while at the same time leaving residual alpha-1,4 linkages that are subject to alpha-amylase attack with attendant liberation of free non-reducing chain terminals that can be attacked by an exocarbohydrase, such as phosphorylase, which serves as a coupling enzyme in the following enzymatic reaction system:

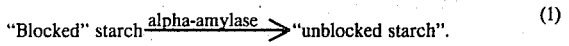
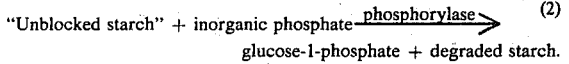
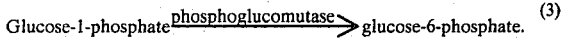
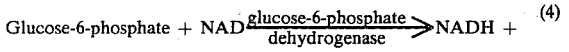

-continued 6-phosphogluconate

The use of "blocked" starch in providing a substrate comprised in a coupled enzymatic reaction system is attended with inherent disadvantages in that, in producing the blocked starch substrate, the oxidation of the starch is only partial and damages alpha-1,4 linkages randomly throughout the starch molecule. As a result, difficulties are encountered as regards controlling the uniformity of the substrate and its reactivity with alpha-amylase and, as a corollary, correctly indicating the rate of change in absorbency occasioned by alpha-amylase in a body fluid. Moreover, because of the reduced overall activity occasioned by the partial oxidation, the amount of the "blocked" starch required for accomplishing a given change in absorbence is undesirably large and substantially interferes with the sensitivity of the test determination.

SUMMARY OF THE INVENTION

It is an object of this invention to provide for use, in determining the concentration of alpha-amylase in a body fluid, an improved enzymatic reagent system that is responsive to the presence of alpha-amylase in a body fluid. It also is an object of this invention to provide a new reagent composition for use in said system and an improved substrate for alpha-amylase for use in the reagent system.

Further objects of the invention relate to improvements whereby the concentration of alpha-amylase in a body fluid may be determined by a kinetic assay employing a coupled enzymatic reaction system, such that a high degree of sensitivity and of uniformity in result may be afforded, while at the same time providing an assay that is relatively simple to carry out, that is rapid, and which does not require the employment of a specimen blank.

DETAILED DESCRIPTION OF THE INVENTION

In accordance with this invention, these and other objects of the invention are obtained by performing the alpha-amylase assay by reacting a maltodextrin phosphorylase limit dextrin with alpha-amylase in the presence of maltodextrin phosphorylase, with resultant formation of fragments of limit dextrin which concomitantly react with the maltodextrin phosphorylase to form the initial component of a coupled enzymatic reaction system that is specific for said component, and which results in the formation of a chromophore, simultaneously performing the reactions of said coupled enzymatic reaction system responsive to the formation of said component, and measuring the rate of formation of said chromophore, said alpha-amylase being rate limiting.

Starch consists in nature of a combination of two polymers, namely, alpha-amylose and amylopectin. Alpha-amylose consists essentially of long unbranched chains in which all of the D-glucose units are bound by alpha-1,4 linkages, namely, linkages which contain an oxygen atom and which link the first carbon atom of a glucose unit with the fourth carbon atom of an immediately adjacent glucose unit. The chains are polydisperse and vary in molecular weight from a few thousand to around 50,000, there being a free, namely unlinked, non-reducing terminal at one end and a free reducing terminal at the other end.

Amylopectin, unlike amylose, is highly branched. In a typical amylopectin, the branches or chains contain, on the average, twelve glucose units successively connected by alpha-1,4 linkages, so that branch points occur on the average of every twelfth glucose unit. At the branch points the chains of alpha-1,4 linked glucose units are linked respectively to the first, fourth and sixth atoms of a single glucose unit, the occurrence of the 1–6 linkage with the sixth carbon atom being the characterizing structural feature at the branch points. The molecular structure of amylopectin normally comprises at its periphery a multiplicity of branches that are linked at one end to branch points and that have a free non-reducing terminal at the remote end with the exception of a single branch that has a free reducing terminal at the remote end. Amylopectin is further characterized by a polysaccharide core comprised of multiplicity of chains and branches made up of alpha-1,4 linked glucose units, which chains interconnect and are terminally linked at each end to branch points and, therefore, do not have a free non-reducing terminal or a free reducing terminal.

When amylose is hydrolyzed by the action thereon of alpha-amylase, the resulting cleavage of the alpha-1,4 linkages may occur anywhere along the amylose chain in such a way as to ultimately yield a mixture of oligosaccharides and maltose. Because of its ability to cleave interior linkages as well as linkages occurring near free non-reducing terminals it is referred to as an endo-carbohydrase. Amylose may also be attacked by enzymes known as exo-carbohydrases, such as beta-amylase, glucoamylase and various phosphorylases. These enzymes cleave away successive carbohydrate monomers beginning only at a free non-reducing terminal of a chain of successive alpha-1,4 linked glucose units.

Because of its branched molecular structure, amylopectin is attacked in different ways by alpha-amylase and by exo-carbohydrases. Exo-carbohydrases cannot hydrolyze the alpha-1,6 linkages that occur at the branch points. Alpha-amylase, being an endo-carbohydrase, has the capacity to cleave alpha-1,4 linkages not only near free non-reducing chain terminals but also randomly at alpha-1,4 linkages between the chain terminals in the interior core portion of amylopectin. Exo-carbohydrases, on the other hand, can only attack alpha-1,4 linked glucopolysaccharides that contain free non-reducing terminals so as to cleave off a carbohydrate monomer followed by successively cleaving off additional monomers while progressing toward the alpha-1,6 branch point of an attacked branch. Eventually the enzymatic activity of an exo-carbohydrase on starch will cease.

The molecularly large carbohydrate product that results from the exhaustive reaction of amylopectin with an exo-carbohydrase is known in the art as a limit dextrin. In general, the structure of the limit dextrin may be considered as being an amylopectin core comprising alpha-1,6 branch sites interconnected by chains of alpha-1,4 glucose that are terminally linked to the alpha-1,6 branch sites. However, the ability of various exo-carbohydrases to attack the chains having free non-reducing terminals varies; as a consequence, depending upon the exo-carbohydrase employed, the amylopectin core will have attached to it short residual alpha-1,4 glucose chains of differing lengths. That is, the limit dextrin obtained with one exo-carbohydrase, e.g., beta-amylase, is not identical to a limit dextrin obtained with another exo-carbohydrase, e.g., maltodextrin phosphorylase. For example, beta-amylase is less effective than maltodextrin phosphorylase in attacking the alpha-1-4 linked glucose chains. Accordingly, the limit dextrin obtained with beta-amylase has longer residual chains than the limit dextrin obtained with maltodextrin phosphorylase. As one consequence of this differing enzyme activity, the limit dextrin obtained with beta-amylase, although no longer capable of acting as a substrate for beta-amylase, is capable of acting as a substrate for maltodextrin phosphorylase. On the other hand, the limit dextrin obtained with maltodextrin phosphorylase cannot act as a substrate for either beta-amylase or maltodextrin phosphorylase. The limit dextrin which is employed in accordance with this invention is one which will not serve as a substrate for maltodextrin phosphorylase, and will be referred to herein as "maltodextrin phosphorylase limit dextrin", or more simply as "MDP limit dextrin".

The MDP limit dextrin employed in accordance with this invention need not necessarily be prepared from starch; for example, it may be produced from glycogen, which is a storage polysaccharide found in animal tissues, being especially abundant in liver and muscle. Glycogen is similar to amylopectin in that it is a polysaccharide characterized by chains of alpha-1,4 linked glucose units. However, it is more highly branched with alpha-1,6 branch points occurring at intervals of about 8 to 10 glucose units. As in the case of amylopectin, glycogen contains chains of alpha-1,4 linked glucose units which chains have their terminal extremities linked to the branch points. Accordingly, when glycogen is exhaustively treated with an exo-carbohydrase, the resulting product is a limit dextrin essentially similar to that produced from starch with that exo-carbohydrase.

In accordance with this invention, MDP limit dextrin is employed as the substrate for alpha-amylase comprised in a specimen to be analyzed, such as a sample of serum or urine, thereby initiating a series of reactions resulting in a chromophore response, the amount of the alpha-amylase being rate limiting and the rate of chromophore response being a measure of the concentration of the alpha-amylase in the specimen.

It is a further feature of this invention that the attack of the alpha-amylase on the MDP limit dextrin substrate therefor occurs in the presence of maltodextrin phosphorylase. It is inherent from the molecular structure of MDP limit dextrin, that the attack on it by alpha-amylase in the specimen is limited essentially to ruptures of the chains of alpha-1,4 linked glucose units that have their terminal extremities linked to the alpha-1,6 branch points therein, with formation of polysaccharide or oligosaccharide fragments of MDP limit dextrin having newly formed free non-reducing chain terminals which are available for reaction with the maltodextrin phosphorylase. The maltodextrin phosphorylase is provided in excess and in sufficient amount to keep the alpha-amylase in the specimen being analyzed as the rate limiting constituent, whereby, as each new free non-reducing terminal is formed, it is attacked by the maltodextrin phosphorylase. Since the rate at which the non-reducing terminals are newly formed is responsive to the rate-limiting concentration of the alpha-amylase in the specimen, it follows that the rate of formation of the reaction products resulting from the attack of the maltodextrin phosphorylase on the non-reducing terminals as they are formed likewise is responsive to the rate limiting concentration of the alpha-amylase specimen.

As is well known, maltodextrin phosphorylase can be derived from mutant *E. coli.* See, e.g., Buehner, "Crystallization and Crystallographic Data of *Escherichia Coli* Maltodextrin Phosphorylase," FEBS Letters, Vol. 85, No. 1, 914 (1978) and Thanner et al, "Hydrophobic and Biospecific Chromatography in the Purification of Maltodextrin Phosphorylase from *E. Coli*", FEBS Letters, Vol. 55, No. 1, 178 (1975). However, maltodextrin phosphorylase obtained from other sources may be used in the practice of this invention.

Maltodextrin phosphorylase is used in the presence of inorganic phosphate, and it reacts with alpha-amylase fragmented MDP limit dextrin to form glucose-1-phosphate from the newly exposed non-reducing ends as and to the extent that the limit dextrin is attacked by alpha-amylase comprised in the specimen. The rate of formation of glucose-1-phosphate may be measured by any suitable coupled enzymatic reaction system. The preferred enzymatic reaction system that is employed is as follows:

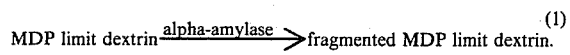
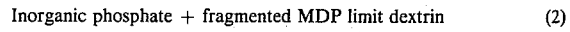
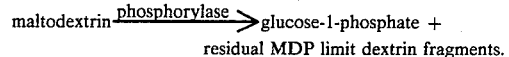
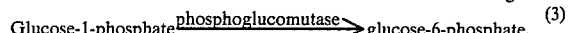
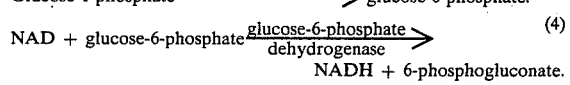

The inorganic phosphate used as a source of phosphate ions may be conveniently supplied by performing the reaction in an aqueous medium containing a phosphate buffer.

The amounts of the respective enzymatic reagents should be such that the alpha-amylase is the rate limiting constituent. NAD is the chromophore forming agent and the rate of its conversion to NADH provides a quantitative measure of the concentration of the alpha-amylase in the specimen. The rate of such conversion normally is measured by measuring the rate of change in absorbence of light of given wave length using an instrument such as a spectrophotometer.

It is a significant advantage of this invention that the enzymatic reactions occurring in the above-mentioned reaction system are essentially unaffected by the presence of the maltose, or other saccharides, such as glucose, which may be present in the specimen, or which may be present in the reagents. For example, carbohydrates such as maltose can be employed as stabilizers or fillers for lyophilized enzyme reagents without effect on the analytical procedure of this invention.

The reactions ordinarily are performed when the reaction system is at a temperature between 18° C. and 40° C. and the pH is between 5 and 8. So long as the alpha-amylase is the rate limiting component of the system the concentrations of the other components are not critical. The reactions occur simultaneously and are triggered by the introduction of the alpha-amylase containing specimen into the aqueous medium containing the other reaction components.

One of the principal advantages of this invention is that the MDP limit dextrin is prepared by a relatively simple and inexpensive procedure which provides a substrate that meets specifications with a high degree of uniformity. Basically the preparation of the limit dextrin comprises incubating the selected carbohydrate with maltodextrin phosphorylase in an aqueous medium in the presence of inorganic phosphate, until the action of the phosphorylase has become exhaustive, and then heating the aqueous medium to boiling to destroy the phosphorylase. Preferably the initial incubation is performed when the aqueous medium is at a temperature of about 37° C. Since the reaction is enzymatically induced, the concentration of the phosphorylase is not critical and may be varied over a wide range such as 1 to 20,000 U when used with a solution containing 50 g/liter of starch. However, it is essential to remove the glucose-1-phosphate formed in the production of the MDP limit dextrin before it can be used in the assay reaction system. This may be accomplished by dialysis.

Ordinarily the carbohydrate from which the limit dextrin is produced is starch in the form that is referred to in the art as soluble starch, namely, starch that has been heated with acid followed by removal of most of the amylose.

As has been noted above, the limit dextrin formed by exhaustive reaction upon soluble starch or other carbohydrate source using beta-amylase is not identical with that formed using maltodextrin phosphorylase in the presence of inorganic phosphate since, as between these exo-carbohydrases, the final extent of the cleavage starting with non-reducing chain terminals is not identical. It is an additional feature of this invention that the MDP limit dextrin used in the assay preferably is produced in a two step process wherein the starch is initially incubated with beta-amylase followed by incubation with maltodextrin phosphorylase in the presence of inorganic phosphate. It has been found that when the limit dextrin is produced in this way the accuracy of the assay is substantially improved. This is because the majority of the cleavage of the carbohydrate source is effected by beta-amylase, and maltose is the major "by-product" of this reaction. Since maltose does not affect the analysis, presence of maltose as an impurity is not a particular problem. On the other hand, the glucose-1-phosphate "by-product" formed by incubation of the carbohydrate source with maltodextrin phosphorylase, can materially interfere with the analysis. Thus, use of maltodextrin phosphorylase only as the final step in the production of MDP limit dextrin reduces the amount of glucose-1-phosphate which is formed, and minimizes the amount of purification of the MDP limit dextrin which is required before use in accordance with this invention.

The MDP limit dextrin as initially produced in an aqueous medium may be employed by adding it to the aqueous medium comprising the remaining components of the overall reaction system of the assay. For convenience in handling, the MDP limit dextrin may be reduced to the solid state by lyophilizing. It may be lyophilized per se or in combination with one or more components of the reaction system that is employed. When employed in combination, the basic combination used in any of the reaction system is the MDP limit dextrin with the maltodextrin phosphorylase. To the basic combination there may be added any one or more of the rest of the components of the selected coupled enzymatic reaction system. Preferably, all the rest of the reaction components are present in the lyophilized state so that at the time the assay is performed all that is required is the addition of water to form the aqueous medium of desired concentration and pH to which the alpha-amylase specimen may be added when the aqueous medium is at the desired temperature. However, if desired, the various components, either individually or in subcombinations, may be provided as contained in a kit for admixture at the time the assay is carried out, to the end that the involved coupled reactions may occur simultaneously so as to form the chromophore at a rate which is limited by the alpha-amylase that is added to complete the reagent system and thereby trigger the involved reactions.

The following example is illustrative of preferred practice of the invention. The following combination is initially prepared:

| | |
|---|---|
| Starch solution | 50g/liter |
| Phosphate buffer | 50mM |
| Beta-amylase | 7200 U. |
| pH | 6.9 |

The foregoing composition is incubated for 18 hours at 37° C. 2100 U. of maltodextrin phosphorylase then is added and incubation is continued at 37° C. for 24 hours. Thereafter, heat to boiling to destroy the beta-amylase and the phosphorylase, and then dialyze to remove glucose-1-phosphate.

Using MDP limit dextrin prepared as above exemplified, the following assay composition is provided:

A. Reaction Composition

| Component | Preferred Range | Optimum Combination |
|---|---|---|
| MDP limit dextrin | 0.1–20mg/ml | 3 mg/ml |
| maltodextrin phosphorylase | 1–10 U/ml | 3 U/ml |
| phosphoglucomutase | 0.1–10 U/ml | 2 U/ml |
| glucose-6-phosphate dehydrogenase | 0.5–10 U/ml | 2 U/ml |
| NAD | 0.1–10 mM | 5 mM |
| phosphate buffer | 10–500 mM | 10 mM |
| glucose-1,6-diphosphate | 0.001–0.1 mM | 0.01 mM |
| magnesium chloride | 0.2–50 mM | 50 mM |
| ethylene diamine tetraacetic acid | 0.1–50 mM | 5 mM |
| pH | 5–8 | 6.9 |

B. Reaction Conditions 1.0 ml of the reaction composition is incubated to 30° C. Add 0.01 ml of alpha-amylase specimen in the form of plasma, serum or urine, mix and record the change in absorbence at 340 nm for 10 minutes using an instrument such as a spectrophotometer. Prepare a curve of change in absorbence per unit time as defined by readings during this period and based on the linear portion of the curve calculate alpha-amylase activity follows:

$$U/l \text{ alpha-amylase} = \frac{\Delta A\ 340/\text{min.} \times 1000 \times V_t \times 1000}{6220 \times L.P. \times V_s}$$

when
$\Delta A\ 340$ = change in absorbence at 340 nm
min = minute
$V_t$ = total volume = 1.01 ml
$V_s$ = sample volume = 0.01 ml
L.P. = light path length — 1.0 cm $U/l$ alpha-amylase = $16,238 \times \Delta A 340/\text{min.}$ Each unit of alpha-amylase activity is defined as that amount of enzyme which catalyzes the production of 1 μmole of NADH per minute at 30° C. The described assay is linear to 1000 U/1.

In carrying out the foregoing example the specimen volume may be varied, e.g., from 0.001 to 0.1 ml per ml of reagent, depending on the sensitivity required and the capability of the instrument used to measure the rate.

In the foregoing formulation, magnesium chloride is a preferred ingredient which is included in order to promote the activity of the maltodextrin phosphorylase by modifying the activity of the phosphoglucomutase so as to promote the enzymatic activity of the phosphorylase. Other cations such as manganese, cobalt, zinc or nickel may be employed for similar purpose. The ethylene diamine tetraacetic acid is preferably included in the composition because of its influence in controlling relative concentrations of divalent cations required for the coupled enzymatic reactions. Glucose-1,6-diphosphate is included in the composition as a co-factor influencing the conversion of glucose-1-phosphate to glucose-6-phosphate in the presence of phosphoglucomutase. Since it also appears to influence the activity of maltodextrin phosphorylase, it should be present in an amount sufficient to activate both enzymes. The composition of the preferred example may also be provided in the lyophilized state wherein the components are present in like relative proportions adapted to provide the concentrations as above given upon reconstitution with water and preferably is supplied in this way for use in clinical testing laboratories that use either manual or mechanized assay techniques. However, the individual components singly or in various subcombinations may be supplied for like purpose and in like relative amounts in the form of a kit.

What is claimed is:

1. An alpha-amylase assay which comprises:
   (a) reacting maltodextrin phosphorylase limit dextrin with an alpha-amylase specimen in the presence of maltodextrin phosphorylase and inorganic phosphate to form limit dextrin fragments which concomitantly react with said maltodextrin phosphorylase to form glucose-1-phosphate as the initial component of a coupled enzymatic reacting system that is specific thereto and that results in the formation of a chromophore;
   (b) simultaneously performing the reactions of said coupled enzymatic reaction system responsive to the formation of said component; and
   (c) measuring the rate of formation of said chromophore;
   wherein the proportions of said limit dextrin, said phosphorylase and said phosphate to said alpha-amylase being such that the amount of said alpha-amylase is rate limiting and wherein said limit dextrin is prepared by the exhaustive treatment of glycogen or starch with maltodextrin phosphorylase or first with β-amylase and then with maltodextrin phosphorylase.

2. An alpha-amylase assay according to claim 1 wherein the performance of said coupled enzymatic reaction system comprises converting said glucose-1-phosphate to glucose-6-phosphate in the presence of phosphoglucomutase, and converting said glucose-6-phosphate to 6-phosphogluconate in the presence of glucose-6-phosphate dehydrogenase and the coenzyme NAD with concomitant conversion of said NAD to NADH.

3. An alpha-amylase assay according to claim 2 wherein the reagent system also contains ethylene diamine tetraacetic acid, glucose-1,6-diphosphate and a cation selected from the group consisting of magnesium, manganese, zinc, nickel and cobalt.

4. A reagent system for an alpha-amylase assay comprising:
   (a) maltodextrin phosphorylase limit dextrin that is the substrate for said alpha-amylase and that is fragmentable by said alpha-amylase to form limit dextrin fragments;
   (b) maltodextrin phosphorylase;
   (c) inorganic phosphate; and
   (d) a coupled enzymatic reaction system for forming a chromophore, which enzymatic reaction system is specific for and responsive to glucose-1-phosphate that is formed by reaction between said phosphorylase and said limit dextrin fragments in the presence of said inorganic phosphate;
   wherein the amounts of said limit dextrin, said phosphorylase, said phosphate and said coupled enzymatic system being such that, when said reagent system is admixed with a specimen containing alpha-amylase, said limit dextrin is fragmented by alpha-amylase to form limit dextrin fragments which react with said phosphorylase to form glucose-1-phosphate, and whereby the amount of alpha-amylase contained in the specimen to be assayed is rate limiting and wherein said limit dextrin is prepared by the exhaustive treatment of glycogen or starch with maltodextrin phosphorylase or first with β-amylase and then with maltodextrin phosphorylase.

5. A reagent system according to claim 4 wherein said enzymatic reaction system comprises phosphoglucomutase, glucose-6-phosphate dehydrogenase, phosphate buffer and NAD.

6. A reagent system according to claim 5 which also comprises ethylene diamine tetraacetic acid, glucose-1,6-diphosphate, and a cation selected from the group consisting of magnesium, manganese, zinc, nickel and cobalt.

7. A reagent system according to claim 4 wherein the MDP limit dextrin is produced by incubating beta-amylase and a carbohydrate selected from the group consisting of starch and glycogen and mixtures thereof in an aqueous medium at a temperature suitable for beta-amylase incubation and until enzymatic action ceases, thereby forming a beta-amylase limit dextrin, followed by further incubating the beta-amylase limit dextrin with maltodextrin phosphorylase in the presence of inorganic phosphate at a temperature suitable for beta-amylase incubation and until enzymatic action ceases, thereby forming MDP limit dextrin, and destroying said beta-amylase and said phosphorylase after said incubations therewith by heating said aqueous medium.

8. A lyophilized reagent system for an alpha-amylase assay according to the reagent system set forth in claim 4.

9. A reagent composition for use in an alpha-amylase assay comprising:
   (a) maltodextrin phosphorylase limit dextrin fragmentable by said alpha-amylase to form limit dextrin fragments comprising non-reducing chain terminals;

(b) maltodextrin phosphorylase in effective amount to react with the chains having said non-reducing terminals comprised in said limit dextrin fragments with resultant formation of glucose-1-phosphate; and (c) inorganic phosphate and wherein said limit dextrin is prepared by the exhaustive treatment of glycogen or starch with maltodextrin phosphorylase or first with β-amylase and then with maltodextrin phosphorylase.

10. A non-aqueous reagent composition for use in an alpha-amylase assay which when dissolved in water will produce an aqueous reagent system as set forth in claim 9.

11. An aqueous composition for use in an alpha-amylase assay comprising:

| | |
|---|---|
| MDP limit dextrin | 0.1–20 mg/ml |
| maltodextrin phosphorylase | 1–10 U/ml |
| phosphoglucomutase | 0.1–10 U/ml |
| glucose-6-phosphate dehydrogenase | 0.5–10 U/ml |
| NAD | 0.1–10 m M |
| phosphate buffer | 10–500 m M |
| glucose-1, 6-diphosphate | 0.001–0.1 m M |
| magnesium chloride | 0.2–100 m M |
| ethylenediamine tetraacetic acid | 0.1–50 m M |
| pH | 5–8 | wherein the pH is adjusted with buffer to a value within a range of 5 to 8 and said limit dextrin is prepared by the exhaustive treatment of starch or glycogen with maltodextrin phosphorylase or first with β-amylase and then with maltodextrin phosphorylase.

12. A lyophilized composition reconstitutable with water to provide the aqueous composition defined in claim 11.

13. An aqueous composition according to claim 11 wherein the MDP limit dextrin is produced by incubating beta-amylase and a carbohydrate selected from the group consisting of starch and glycogen and mixtures thereof in an aqueous medium at a temperature suitable for beta-amylase incubation and until enzymatic action ceases, thereby forming a beta-amylase limit dextrin, followed by further incubating the beta-amylase limit dextrin with maltodextrin phosphorylase in the presence of inorganic phosphate at a temperature suitable for phosphorylase incubation and until enzymatic action ceases, thereby forming MDP limit dextrin, and destroying said beta-amylase and said phosphorylase after said incubations therewith by heating said aqueous medium.

14. A lyophilized composition reconstitutable with water to provide the aqueous composition defined in claim 13.

* * * * *

UNITED STATES PATENT AND TRADEMARK OFFICE
CERTIFICATE OF CORRECTION

PATENT NO. : 4,304,854
DATED : December 8, 1981
INVENTOR(S) : Paul T. Nix et al.

It is certified that error appears in the above—identified patent and that said Letters Patent is hereby corrected as shown below:

Column 2, line 52, after "linkages", change "in" to -- is --.

Signed and Sealed this

Fourth Day of May 1982

[SEAL]

Attest:

GERALD J. MOSSINGHOFF

Attesting Officer

Commissioner of Patents and Trademarks